United States Patent [19]  [11] Patent Number: 4,558,055
Seidel et al.  [45] Date of Patent: Dec. 10, 1985

[54] VASO-DILATING 1,4-DIHYDROPYRIDINE LACTAMS

[75] Inventors: Wolfgang Seidel; Stanislav Kazda; Andreas Knorr, all of Wuppertal, Fed. Rep. of Germany

[73] Assignee: Bayer Aktiengesellschaft, Leverkusen, Fed. Rep. of Germany

[21] Appl. No.: 531,361

[22] Filed: Sep. 12, 1983

[30] Foreign Application Priority Data

Sep. 23, 1982 [DE] Fed. Rep. of Germany ....... 3235221

[51] Int. Cl.$^4$ ............. C07D 491/044; C07D 491/056; A61K 31/455
[52] U.S. Cl. ..................................... 514/291; 546/89; 546/90
[58] Field of Search ..................... 546/89, 90; 514/291

[56] References Cited

U.S. PATENT DOCUMENTS 4,478,834 10/1984 Shroff et al. ......................... 546/89

FOREIGN PATENT DOCUMENTS 0055488 4/1983 Japan ..................................... 546/89

— OTHER PUBLICATIONS

Schram, M., Nature, vol. 303, Jun. 1983.
Bossert, F., Agnew. Chem. Int. Ed. England 20, 762–769, (1981).

*Primary Examiner*—Henry R. Jiles
*Assistant Examiner*—Dale A. Bjorkman
*Attorney, Agent, or Firm*—Sprung Horn Kramer & Woods

[57] ABSTRACT

Circulation-active novel ring-bridged 1,4-dihydropyridines of the formula

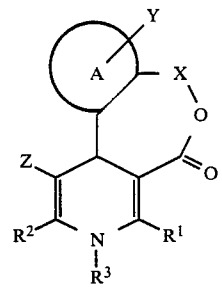

in which

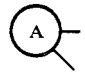

is an aryl or heterocyclic radical,
X is an alkyl or alkoxy radical, and
Z is a carboxylic or sulphonic acid ester radical,
or pharmaceutically acceptable acid addition salts thereof, which affect the circulatory system.

12 Claims, No Drawings

VASO-DILATING 1,4-DIHYDROPYRIDINE LACTAMS

The invention relates to new, ring-bridged 1,4-dihydropyridines, processes for their preparation and their use in medicaments, in particular medicaments which influence the circulation.

It has already been disclosed that diethyl 1,4-dihydro-2,6-dimethyl-4-phenyl-pyridine-3,5-dicarboxylate is obtained when ethyl benzylideneacetoacetate is reacted with ethyl β-aminocrotonate or ethylacetoacetate and ammonia E. Knoevenagel, Ber. dtsch. chem. Ges. 31, 743 (1898).

It is also known that certain 1,4-dihydropyridines have interesting pharmacological properties and are used, in particular, as agent which influence the circulation (F. Bossert, W. Vater, Naturwissenschaften 58, 578 (1971) and DOS (German Published Specification) 2,117,571).

In contrast, the ring-bridged dihydropyridines described in the following text are new.

The invention relates to new 1,4-dihydropyridines of the general formula I

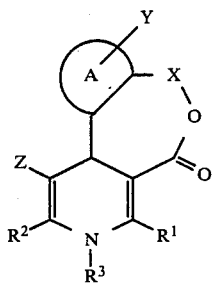

in which

represents aryl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, benzoxadiazolyl, quinazolyl or quinoxalyl, Y represents one or two identical or different substituents from the group comprising alkyl, alkenyl, alkinyl, alkoxy, alkenoxy, aryloxy, aralkoxy, alkinoxy, phenyl, halogen, alkylene, dioxyalkylene, trifluoromethyl, trifluoromethoxy, nitro, cyano, azido, carboxyl, hydroxyl, amino, alkylamino, halogenoalkoxy, carbalkoxy, carboxamido, sulphonamido, $SO_m$-alkyl, $SO_m$-aryl and $SO_m$-aralkyl (m=0, 1, 2), X represents a straight-chain or branched alkyl chain which has up to 20 carbon atoms, is linked to

directly or via an oxygen, sulphur or nitrogen atom and can optionally be interrupted by one or more oxygen atoms, nitrogen atoms or

groups, it being possible for the above-mentioned nitrogen atoms to be substituted by H, alkyl, acyl or benzyl, Z (a) represents the group —COOR$^4$, wherein R$^4$ represents a straight-chain, branched or cyclic, saturated or unsaturated hydrocarbon which can be interrupted in the chain by oxygen, sulphur or the —SO$_2$— group and which is optionally substituted by halogen, cyano, pyridyl, phenyl, phenoxy, phenylthio or phenylsulphonyl, it being possible for the phenyl groups in turn to be substituted by halogen, cyano, dialkylamino, alkoxy, alkyl, trifluoromethyl or nitro, or it being possible for the hydrocarbon radical to be substituted by an amino group, this amino group being substituted by two identical or different substituents from the group comprising alkyl, alkoxyalkyl, aryl and aralkyl, or the amino group being substituted such that 2 substituents, together with the nitrogen atom, form a 5-membered to 7-membered ring, which can contain, as a further hetero-atom, oxygen or sulphur or an N-alkyl grouping, or Z (b) represents the group SO$_2$—R$^5$, wherein R$^5$ denotes a straight-chain branched or cyclic saturated or unsaturated aliphatic hydrocarbon radical, which is optionally interrupted by one oxygen in the chain and is optionally substituted by phenyl, phenoxy, phenylthio, phenylsulphonyl, pyridyl or amino, the aryl radicals mentioned being in turn optionally substituted by halogen, cyano, dialkylamino, alkoxy, alkyl, trifluoromethyl or nitro, and the amino group optionally being substituted by two identical or different substituents from the group comprising alkyl, alkoxyalkyl, aryl and aralkyl, or 2 of these substituents optionally forming, with the nitrogen atom, a 5-membered to 7-membered ring which can contain, as a further hetero-atom, oxygen, sulphur or the N-alkyl grouping, or wherein R$^5$ denotes an aryl radical, which optionally contains 1, 2 or 3 identical or different substituents from the group comprising alkyl, alkoxy, halogen, cyano, trifluoromethyl, trifluoromethoxy, dialkylamino and nitro, or Z (c) represents the group —COR$^6$, wherein R$^6$ denotes an optionally substituted alkyl, aryl or aralkyl radical, or Z (d) represents a nitrile radical, and R$^1$ and R$^2$ are identical or different and each represent hydrogen, a straight-chain or branched alkyl or aryl radical or an aralkyl radical, and R$^3$ represents hydrogen or a straight-chain or branched alkyl radical which is optionally interrupted by an oxygen atom, or an aryl radical or an aralkyl radical, and their pharmaceutically acceptable acid addition salts.

It has been found that the ring-bridged 1,4-dihydropyridines of the general formula I are obtained by a process in which (a) 1,4-dihydropyridines of the formula II, which can be prepared by the processes customary for the synthesis of 1,4-dihydropyridines,

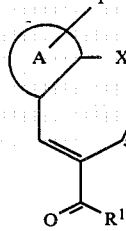

(II)

wherein

,

Y, Z, X, $R^1$, $R^2$ and $R^3$ have the meaning given in formula (I);
are cyclized by methods which are known from the literature; or (b) ylidene-$\beta$-keto esters of the general formula (III)

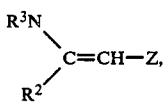

(III)

in which

, $R^1$, X and Y have the abovementioned meaning,
are reacted with enamino compounds of the general formula (IV)

(IV)

in which $R^2$, $R^3$ and Z have the abovementioned meaning,
if appropriate in the presence of inert organic solvents, at temperatures between 20° and 150° C., or (c) ylidene-$\beta$-keto esters of the general formula (III) are reacted with amines of the general formula (V)

$R^3-NH_2$ (V), in which $R^3$ has the abovementioned meaning,
and keto compounds of the general formula (VI)

 (VI)

in which $R^2$ and Z have the abovementioned meaning,
if appropriate in the presence of inert organic solvents, at temperatures between 20° and 150° C.

The ring-bridged 1,4-dihydropyridines of the general formula I according to the invention have valuable pharmacological properties. On the basis of their circulation-influencing action, they can be used as antihypertensive agents, as peripheral and cerebral vasodilators and as coronary therapeutics.

The present invention particularly relates to 1,4-dihydropyridines of the general formula I, in which

represents phenyl, naphthyl, thienyl, furyl, pyrryl, pyridyl, pyrimidyl, quinolyl, isoquinolyl, indolyl, benzimidazolyl or benzoxadiazolyl, Y represents one or two identical or different substituents from the group comprising alkyl, cycloalkyl, alkenyl, alkinyl and alkoxy with in each case up to 7 carbon atoms, dioxymethylene, phenyl, halogen, -S-benzyl, O-benzyl, trifluoromethyl, trifluoromethoxy, nitro, cyano, azido, hydroxyl, mono- and di-alkylamino with in each case 1 to 4 carbon atoms in the alkyl radical, carboxamido, sulphonamido and $SO_m$-alkyl (m=0, 1 or 2; alkyl containing up to 4 carbon atoms), X represents a straight-chain or branched alkyl chain which has up to 20 carbon atoms, is linked with

directly or via an oxygen or sulphur atom and can optionally be interrupted by one or more oxygen atoms or

groups,

Z (a) represents the group $-COOR^4$,
wherein
$R^4$ represents a straight-chain, branched or cyclic, saturated or unsaturated hydrocarbon radical which has up to 8 carbon atoms, is optionally interrupted in the alkyl chain by one oxygen or sulphur atom or the $-SO_2-$ group and is optionally substituted by fluorine, chlorine, bromine, trifluoromethyl, phenyl, phenoxy, phenylthio or phenylsulphonyl, the phenyl radicals in turn optionally being mono- or di-substituted by fluorine, chlorine, bromine, cyano, nitro, trifluoromethyl or alkyl, alkoxy or dialkylamino with in each case 1 to 4 carbon atoms in the alkyl and alkoxy radicals, or the hydrocarbon is optionally substituted by an amino group, this amino group optionally carrying two identical or different substituents from the group comprising alkyl with 1 to 4 carbon atoms, alkoxyalkyl with up to 6 carbon atoms, phenyl, benzyl and phenethyl, or the nitrogen of this amino group forming, with these substituents, a 5-membered to 7-membered ring, which can contain, as a further hetero-atom, an oxygen or sulphur atom or an N-alkyl group with 1 to 4 carbon atoms in the alkyl radical, or Z (b) represents the group $-SO_2-R^5$,
wherein $R^5$ represents a straight-chain, branched, cyclic, saturated or unsaturated aliphatic hydrocarbon radical which has up to 6 carbon atoms, is optionally interrupted in the chain by one oxygen atom and is optionally substituted by phenyl, phenoxy, phenylthio or phenylsulphonyl, the phenyl radicals mentioned being in turn optionally mono- or di-substituted by fluorine, chlorine, bromine, cyano, nitro, trifluoromethyl or alkyl, alkoxy or dialkylamino with in each case 1 to 4 carbon atoms in the alkyl or alkoxy radicals, or the hydrocarbon radical is substituted by an amino group, this amino group carrying two identical or different substituents from the group comprising alkyl and alkoxyalkyl with in each case up to 4 carbon atoms, phenyl, benzyl and phenethyl, or the substituents of this amino group forming, with the nitrogen atom, a 5-membered to 7-membered ring, which can contain, as a further hetero-atom, an oxygen or sulphur atom or the N-alkyl grouping, the alkyl group containing 1 to 3 carbon atoms, or wherein $R^5$ represents a phenyl radical, which is optionally substituted by 1, 2 or 3 identical or different substituents from the group comprising nitro, cyano, trifluoromethyl, trifluoromethoxy, fluorine, chlorine, bromine and alkyl, alkoxy and dialkylamino, the alkyl and alkoxy radicals mentioned each containing 1 to 4 carbon atoms, or Z (c) represents the group $-COR^6$,
wherein $R^6$ denotes a straight-chain or branched alkyl radical with 1 to 5 carbon atoms, phenyl or benzyl, or Z (d) represents a nitrile radical, and $R^1$ and $R^2$ are identical or different and each represent hydrogen or a straight-chain or branched alkyl radical with 1 to 4 carbon atoms or a phenyl radical or benzyl radical and $R^3$ represents hydrogen or a straight-chain or branched alkyl radical which has 1 to 6 carbon atoms and is optionally interrupted in the alkyl chain by an oxygen, or represents a phenyl or benzyl radical, and their pharmaceutically acceptable acid addition salts.

Compounds which may be particularly singled out are those of the general formula (I) in which

represents phenyl or pyridyl;

Y represents nitro, cyano, trifluoromethyl, trifluoromethoxy, fluorine, chlorine, bromine, azido, alkoxy with up to 4 carbon atoms or O-benzyl, X represents a straight-chain or branched alkyl chain which has up to 12 carbon atoms, is linked to

directly or via an oxygen or sulphur atom and can optionally be interrupted by one or two oxygen atoms, Z (a) represents the group $COOR^4$,
wherein $R^4$ denotes a straight-chain or branched alkyl radical which has 1 to 8 carbon atoms and is optionally substituted by an alkoxy group with up to 4 carbon atoms, by a cyano group, a fluorine group or a chlorine group or by an amino group, which is in turn monosubstituted by alkyl with 1 to 4 carbon atoms and carries, as the third substituent, an identical or different alkyl group with 1 to 4 carbon atoms or a benzyl radical, or Z (b) represents a nitrile radical; and $R^1$ and $R^2$ are identical or different and each represent hydrogen or alkyl with 1 or 2 carbon atoms and $R^3$ represents hydrogen, alkyl with up to 4 carbon atoms or benzyl, and their pharmaceutically acceptable acid addition salts.

With knowledge of the prior art, it could not be predicted that substances which are distinguished by advantageous biological properties are obtained by cyclization between the dihydropyridine ring and its substituents in the 4-position.

It is particularly remarkable that the biological action increases with the size of the newly formed ring.

Because of their unexpected pharmaceutical action, they are an enrichment of the art.

Process Variant A

According to process Variant A, 1,4-dihydropyridines of the formula II are cyclized in the presence of reagents which activate the carboxylic acid group and promote elimination of water or which convert the alcohol group into a better leaving group, under conditions suitable for this, for example in high dilution (E. Haslam, Tetrahedron 36, 2409 (1980); K. C. Nicolaou, Tetrahedron 33, 683 (1977); T. G. Back, Tetrahedron 33, 3041 (1977); and M. A. Ondetti and P. L. Thomas, J. Am. Chem. Soc. 87, 4373 (1965)); or are converted into activated carboxylic acid derivatives by known processes and then reacted intramolecularly, in a second step, with the free hydroxyl group bonded to X, if necessary using an auxiliary suitable for this reaction.

The 1,4-dihydropyridinecarboxylic acids used as starting substances are new and can be prepared by known methods (DT-OS (German Published Specification) 2,847,237).

Of the reagents known from the literature for activating a carboxylic acid or alcohol group, the following may be particularly singled out: trifluoroacetic anhydride, mercury trifluoroacetate, p-toluenesulphonyl chloride, 1,1'-carbonyldiimidazole, 2,2'-dipyridyldisulphide, 2-chloro-1-methylpyridinium iodide, dicyclohexylcarbodiimide, N-trimethylsilylimidazole, N,N-dimethylformamidedinopentylacetal, diethylazodicarboxylate/triphenylphosphine and 1-cyclohexyl-3-(2-morpholinoethyl)carbodiimide metho-p-toluenesulphonate.

Possible diluents are all the suitable organic solvents, with the exception of carboxylic acids and alcohols, preferably ether, such as tetrahydrofuran, diethyl ether, dioxane and glycol dimethyl ether, or acetonitrile, toluene or methylene chloride.

Process Variant B

According to Process Variant B, ylidene-β-keto esters of the general formula III are reacted with enamimo compounds of the general formula IV, if appropriate in the presence of inert organic solvents, preferably glacial acetic acid, methanol, ethanol or tetrahydrofuran.

Process Variant C

According to Process Variant C, ylidene-β-keto esters of the general formula III are reacted with keto compounds of the general formula (VI) and amines of the general formula (V), if appropriate in the presence of inert organic solvents, for example methanol, ethanol, isopropanol, diethyl ether, glacial acetic acid or acetonitrile.

The ylidene-β-keto esters of the formula (III) used as starting substances can be prepared by methods which are known from the literature (G. Jones, "The Koevenagel Condensation", in Org. Reactions Volume XV, 204 et seq. (1967)) with subsequent intramolecular cyclization by the methods described under Process Variant A.

Enamino compounds (IV) used as starting substances are known; they can be prepared by methods which are known from the literature (compare A. C. Cope, J. Am. Chem. Soc. 67, 1017 (1945)).

β-keto compounds (VI) used as starting substances are known; they can be prepared by methods which are known from the literature (for example D. Borrmann, "Umsetzung von Diketen mit Alkoholen, Phenolen und Mercaptanen" ("Reaction of Diketenes with Alcohols, Phenols and Mercaptans"), in Houben-Weyl, Methoden der organischen Chemie (Methods of Organic Chemistry), Volume VII/4, 230 et seq. (1968); and Y. Oikawa, K. Sugano and O Yonemitsu, J. Org. Chem. 43, 2087 (1978)).

The reaction temperatures can be varied within a substantial range in all the process variants. In general, the reaction is carried out between 20° and 150° C., but preferably at the boiling point of the particular solvent, and occasionally at temperatures between +20° and −20° C.

The reaction can be carried out under normal pressure, but also under increased pressure. In general, it is carried out under normal pressure.

The above preparation processes are only given for illustration, and the preparation of the compounds of the formula (I) is not limited to these processes, but any modification of these processes is applicable in the same manner to the preparation of the compounds according to the invention.

The compounds according to the invention can exist in stereoisomeric forms which either are mirror images (enantiomers) or are not mirror images (diastereomers).

The present invention relates both to the antipodes and to the diastereomer mixtures. The racemic forms can be separated into the stereoisomerically pure constituents, as can the diastereomers, in a known manner (compare, for example, E. L. Eliel, Stereochemistry of Carbon Compounds, McGraw Hill, 1962).

Examples which may be mentioned of compounds according to the invention are: 1,4-dihydro-2,6-dimethyl-4-(2-(5-hydroxypentoxy)phenyl)-pyridine-3-butoxycarbonyl-5-carboxylic acid lactone, 1,4-dihydro-2,6-dimethyl-4-(2-(3-hydroxypropoxy)-3-nitrophenyl)-pyridine-3-isopropoxycarbonyl-5-carboxylic acid lactone, 1,4-dihydro-2,6-dimethyl-4-(2-(4-hydroxybutoxy)-5-nitrophenyl)-pyridine-3-octyloxycarbonyl-5-carboxylic acid lactone, 1,4-dihydro-2,6-dimethyl-4-(2-(3-hydroxypropoxy)-3-methoxyphenyl)-pyridine-3-butoxycarbonyl-5-carboxylic acid lactone, 1,4-dihydro-2,6-dimethyl-4-(2-(4-hydroxybutoxy)-5-chlorophenyl)-pyridine-3-methoxycarbonyl-5-carboxylic acid lactone, 1,4-dihydro-2,6-dimethyl-4-(2-(hydroxyethyl)phenyl)-pyridine-3-propoxycarbonyl-5-carboxylic acid lactone, 1,4-dihydro-2,6-dimethyl-4-(2-(11-hydroxyundecyloxy)phenyl)-pyridine-3-octyloxycarbonyl-5-carboxylic acid lactone and 1,4-dihydro-2,6-dimethyl-4-(2-(4-hydroxybutoxy)-phenyl)-pyridine-3-methoxycarbonyl-5-carboxylic acid lactone.

The compound of the general formula (I) exhibit interesting biological actions. They have a broad and diverse pharmacological action spectrum. The following main actions may be mentioned specifically:

1. On parenteral, oral and perlingual administration, the compounds effect distinct dilation of the coronary vessels. This action on the coronary vessels is intensified by a simultaneous nitrite-like effect of reducing the load on the heart.

They influence or modify cardiac metabolism in the sense of an energy saving.

2. The excitability of the stimulus formation and excitation conduction system within the heart is lowered, so that an antifibrilation action which can be demonstrated at therapeutic doses results.

3. The tone of the smooth muscle of the vessels is greatly reduced under the action of the compounds. This vascular-spasmolytic action can take place in the entire vascular system or can manifest itself more or less isolated in circumscribed vascular regions (such as, for example, in the brain).

4. The compounds lower the blood pressure of normotonic and hypertonic animals and can thus be used as antihypertensive agents.

5. The compounds have powerfully muscular-spasmolytic actions which manifest themselves on the smooth muscle of the stomach, the intestinl tract, the urogenital tract and the respiratory system.

The new active compounds can be converted in a known manner into the customary formulations, such as tablets, capsules, dragees, pills, granules, aerosols, syrups, emulsions, suspensions and solutions, using inert non-toxic, pharmaceutically suitable excipients or solvents. The therapeutically active compound should in each case be present in a concentration of about 0.5 to 90% by weight of the total mixture, that is to say in amounts which suffice to achieve the dosage range indicated.

The formulations are prepared, for example, by extending the active compounds with solvents and/or excipients, optionally with the use of emulsifiers and/or dispersing agents, and, for example when using water as a diluent, organic solvents can optionally be used as auxiliary solvents.

Examples of auxiliary substances which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid excipients, such as, for example, natural rock powders (for example kaolins, aluminas, talc and chalk), synthetic rock powders (for example highly disperse silica and silicates) and sugars (for example raw sugar, lactose and glucose), emulsifiers (for example polyoxyethylene fatty acid esters, polyoxyethylene fatty alcohol ethers, alkylsulphonates and arylsulphonates), dispersing agents (for example lignin sulphite waste liquors, methylcellulose, starch and polyvinylpyrrolidone) and lubricants (for example magnesium stearate, talc, stearic acid and sodium lauryl-sulphate).

Administration is effected in the customary manner, preferably orally or parenterally, in particular perlingually. In the case of oral use, the tablets can, of course, also contain in addition to the excipients mentioned, additives such as sodium citrate, calcium carbonate and dicalcium phosphate, together with various additional substances, such as starch, preferably potato starch, gelatine and the like. Furthermore, lubricants, such as magnesium stearate, sodium lauryl-sulphate and talc, can be co-used when making tablets. In the case of aqueous suspensions and/or elixirs which are intended for oral use, the active compounds can be mixed with various flavor-improving agents or colorants in addition to the abovementioned auxiliary substances.

In the case of parenteral use, solutions of the active compounds, employing suitable liquid excipients, can be used.

In general, it has proved advantageous, in the case of intravenous administration, to administer amounts of about 0.01 to 10 mg/kg, preferably about 0.01 to 5 mg/kg, of body weight daily to achieve effective results, and in the case of oral administration, the dosage is about 0.1 to 50 mg/kg, preferably 0.5 mg to 10 mg/kg, of body weight daily.

Nevertheless, it can at times be necessary to deviate from the amounts mentioned, and in particular to do so as a function of the body weight of the experimental animal or of the nature of the administration method, but also because of the species of animal and its individual behavior towards the medicament, and the nature of the formulation of the medicament and the time or interval over which the administration takes place. Thus it can suffice in some cases to manage with less than the abovementioned minimum amount, while in other cases the upper limit mentioned must be exceeded. Where relatively large amounts are administered, it can be advisable to divide these into several individual administrations over the course of the day. The same dosage range is envisaged for administration in human medicine. The above statements also apply here in the general sense.

PREPARATION EXAMPLES

Example 1

Preparation of 1,4-dihydro-2,6-dimethyl-4-(2-(2-hydroxyethoxy)-phenyl)-pyridine-3-ethoxycarbonyl-5-carboxylic acid lactone.

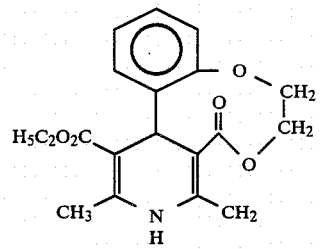

1.5 g (12 mmols) of 4-N,N-dimethylaminopyridine are added to a suspension of 10 g (23.6 mmols) of 1-cyclohexyl-3-(2-morpholinoethyl)carbodiimide metho-p-toluenesulphonate in 200 ml of absolute tetrahydrofuran, and a solution of 5 g (13.3 mmols) of 1,4-dihydro-2,6-dimethyl-4-(2-(2-hydroxyethoxy-phenyl)-pyridine-3-ethoxycarbonyl-5-carboxylic acid in 500 ml of absolute tetrahydrofuran is then added dropwise under nitrogen in the course of 72 hours. The urea formed and excess reagent are filtered off, the solvent is distilled off in vacuo and the residue is recrystallized from ethanol or purified by chromatography.

Melting point: 213° C. Yield: 1.90 g (30%).

The following compounds are prepared analogously to Example 1:

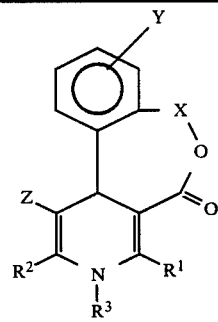

| Example | X | Y | Z | $R^1$ | $R^2$ | $R^3$ | Melting Point | Yield |
|---|---|---|---|---|---|---|---|---|
| 2 | $O(CH_2)_3$— | —H | —$CO_2C_2H_5$ | —$CH_3$ | —$CH_3$ | —H | 186° | 28% |
| 3 | $O(CH_2)_4$— | —H | —$CO_2C_2H_5$ | —$CH_3$ | —$CH_3$ | —H | 165° | 5% |
| 4 | $O(CH_2)_{11}$— | —H | —$CO_2C_2H_5$ | —$CH_3$ | —$CH_3$ | —H | amorphous | 9% |
| 5 | $CH_2$— | —H | —$CO_2C_2H_5$ | —$CH_3$ | —$CH_3$ | —H | 203° | 39% |
| 6 | $CH_2$—$CH_2$— | —H | —$CO_2C_2H_5$ | —$CH_3$ | —$CH_3$ | —H | 196° | 49% |
| 7 | $O(CH_2)_5$— | —H | —$CO_2C_2H_5$ | —$CH_3$ | —$CH_3$ | —H | 169° | 60% |

The compounds can be employed in the same way as the known 1,4-dihydropyridines referred to hereinabove.

It will be understood that the specification and examples are illustrative but not limitative of the present invention and that other embodiments within the spirit and scope of the invention will suggest themselves to those skilled in the art.

What is claimed is:

1. A 1,4-dihydropyridine of the formula

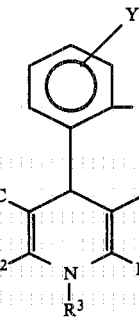

in which
Y represents nitro, cyano, trifluoromethyl, trifluoromethoxy, fluorine, chlorine, bromine, azido, alkoxy with up to 4 carbon atoms or O-benzyl,
X represents a straight-chain or branched alkyl chain which has up to 12 carbon atoms, is linked to its phenyl ring directly or via an oxygen or sulphur atom and can optionally be interrupted by one or two oxygen atoms,
$R^4$ denotes a straight-chain or branched alkyl radical which has 1 to 8 carbon atoms and is optionally substituted by an alkoxy group with up to 4 carbon atoms, by a cyano group, a fluorine group or a chlorine group or by an amino group, which is in turn monosubstituted by alkyl with 1 to 4 carbon atoms and carries, as the third substituent, an identical or different alkyl group with 1 to 4 carbon atoms or a benzyl radical,
$R^1$ and $R^2$ are identical or different and each represent hydrogen or alkyl with 1 or 2 carbon atoms and
$R^3$ represents hydrogen, alkyl with up to 4 carbon atoms or benzyl,
or a pharmaceutically acceptable acid addition salt thereof.

2. A 1,4-dihydropyridine according to claim 1, wherein such compound is 1,4-dihydro-2,6-dimethyl-4-(2-(2-hydroxyethoxy)-phenyl)-pyridine-3-ethoxycarbonyl-5-carboxylic acid lactone of the formula

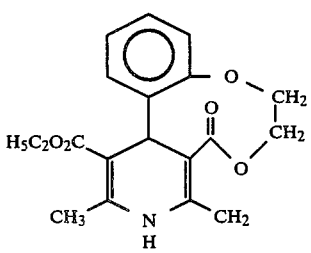

or a pharmaceutically acceptable acid addition salt thereof.

3. A 1,4-dihydropyridine according to claim 1, wherein such compound is 1,4-dihydro-2,6-dimethyl-4-(2-(3-hydroxypropoxy)-phenyl)-pyridine-3-ethoxycarbonyl-5-carboxylic acid lactone of the formula

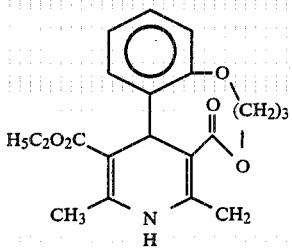

or a pharmaceutically acceptable acid addition salt thereof.

4. A 1,4-dihydropyridine according to claim 1, wherein such compound is 1,4-dihydro-2,6-dimethyl-4-(2-(4-hydroxybutoxy)-phenyl)-pyridine-3-ethoxycarbonyl-5-carboxylic acid lactone of the formula

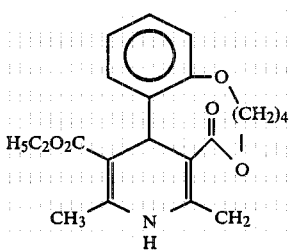

or a pharmaceutically acceptable acid addition salt thereof.

5. A 1,4-dihydropyridine according to claim 1, wherein such compound is 1,4-dihydro-2,6-dimethyl-4-(2-(1-hydroxyundecyloxy)-phenyl)-pyridine-3-ethoxycarbonyl-5-carboxylic acid lactone of the formula

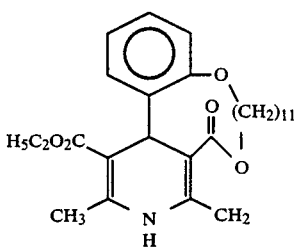

or a pharmaceutically acceptable acid addition salt thereof.

6. A 1,4-dihydropyridine according to claim 1, wherein such compound is 1,4-dihydro-2,6-dimethyl-4-(2-(hydroxymethyl)-phenyl)-pyridine-3-ethoxycarbonyl-5-carboxylic acid lactone of the formula

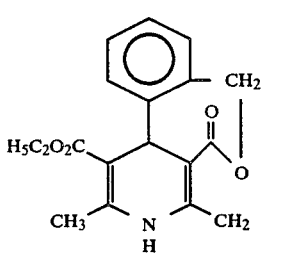

or a pharmaceutically acceptable acid addition salt thereof.

7. A 1,4-dihydropyridine according to claim 1, wherein such compound is 1,4-dihydro-2,6-dimethyl-4-(2-(2-hydroxyethyl)-phenyl)-pyridine-3-ethoxycarbonyl-5-carboxylic acid lactone of the formula

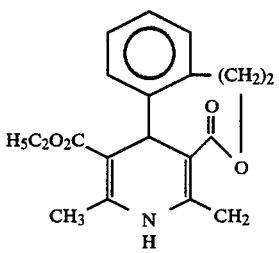

or a pharmaceutically acceptable acid addition salt thereof.

8. A 1,4-dihydropyridine according to claim 1, wherein such compound is 1,4-dihydro-2,6-dimethyl-4-(2-(5-hydroxypentoxy)-phenyl)-pyridine-3-ethoxycarbonyl-5-carboxylic acid lactone of the formula

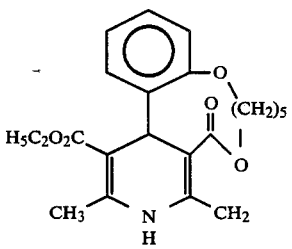

or a pharmaceutically acceptable acid addition salt thereof.

9. A blood pressure lowering, anti-fibrillar and anti-spasmolytic composition comprising an amount effective therefor of a compound or salt according to claim 1 in admixture with a diluent.

10. A unit dose of a composition according to claim 9 in the form of a capsule, tablet or ampule.

11. A method of lowering the blood pressure, defibrillating the heart output and eliminating spasms of a patient which comprises administering to such patient an amount effective therefor of a compound or salt according to claim 1.

12. The method according to claim 11, wherein such compound is
1,4-dihydro-2,6-dimethyl-4-(2-(2-hydroxyethoxy)-phenyl)-pyridine-3-ethoxycarbonyl-5-carboxylic acid lactone,
1,4-dihydro-2,6-dimethyl-4-(2-(3-hydroxypropoxy)-phenyl)-pyridine-3-ethoxycarbonyl-5-carboxylic acid lactone,
1,4-dihydro-2,6-dimethyl-4-(2-(4-hydroxy-butoxy)-phenyl)-pyridine-3-ethoxycarbonyl-5-carboxylic acid lactone,
1,4-dihydro-2,6-dimethyl-4-(2-(1-hydroxy-undecyloxy)-phenyl)-pyridine-3-ethoxycarbonyl-5-carboxylic acid lactone,
1,4-dihydro-2,6-dimethyl-4-(2-(hydroxymethyl)-phenylpyridine-3-ethoxycarbonyl-5-carboxylic acid lactone,
1,4-dihydro-2,6-dimethyl-4-(2-(2-hydroxyethyl)-phenyl)-pyridine-3-ethoxycarbonyl-5-carboxylic acid lactone, or
1,4-dihydro-2,6-dimethyl-4-(2-(5-hydroxy-pentoxy)-phenyl)-pyridine-3-ethoxycarbonyl-5-carboxylic acid lactone,
or a pharmaceutically acceptable acid addition salt thereof.

* * * * *